(12) United States Patent
Kroell (10) Patent No.: US 9,677,743 B2
(45) Date of Patent: Jun. 13, 2017

(54) LIGHTING DEVICE WITH A PUMP LASER ROW AND METHOD FOR OPERATING SAID LIGHTING DEVICE

(71) Applicant: OSRAM GmbH, Munich (DE)

(72) Inventor: Josef Kroell, Potsdam (DE)

(73) Assignee: Osram GmbH, Munich (DE)

( * ) Notice: Subject to any disclaimer, the term of this patent is extended or adjusted under 35 U.S.C. 154(b) by 301 days.

(21) Appl. No.: 14/382,785

(22) PCT Filed: Feb. 14, 2013

(86) PCT No.: PCT/EP2013/053013
§ 371 (c)(1),
(2) Date: Sep. 4, 2014

(87) PCT Pub. No.: WO2013/131730
PCT Pub. Date: Sep. 12, 2013

(65) Prior Publication Data
US 2015/0049457 A1 Feb. 19, 2015

(30) Foreign Application Priority Data
Mar. 5, 2012 (DE) .......................... 10 2012 203 442

(51) Int. Cl.
*F21V 13/08* (2006.01)
*G01N 21/88* (2006.01)
(Continued)

(52) U.S. Cl.
CPC ................ *F21V 13/08* (2013.01); *F21K 9/62* (2016.08); *F21K 9/64* (2016.08); *F21K 9/65* (2016.08);
(Continued)

(58) Field of Classification Search
CPC .... F21Y 2115/30; F21Y 2101/00; F21K 9/62; F21K 9/64; F21K 9/65; F21V 13/08;
(Continued)

(56) References Cited

U.S. PATENT DOCUMENTS 8,853,655 B2 * 10/2014 Bezel .................... H01J 61/025
250/493.1
2005/0152146 A1 * 7/2005 Owen ....................... A61L 2/10
362/294
(Continued)

FOREIGN PATENT DOCUMENTS

WO  03096387 A2  11/2003

OTHER PUBLICATIONS

Search Report issued in the German priority patent application No. DE 10 2012 203 442.0 on Nov. 16, 2012.
International Search Report issued in PCT/EP2013/053013 on Apr. 22, 2013.

*Primary Examiner* — Laura Tso
(74) *Attorney, Agent, or Firm* — Viering, Jentschura & Partner (57) ABSTRACT

A lighting device may include a pump laser row and a phosphor arrangement. The pump laser row is designed for the purpose of emitting pump laser radiation for the irradiation of the phosphor arrangement. The phosphor arrangement has at least two different phosphors, which can be irradiated with the pump laser radiation and emit the pump laser radiation again at least partially and converted in wavelength differently in each case, and a movable mirror, which is designed for the purpose of reflecting the pump laser radiation of the pump laser row in a targeted manner on the phosphors in dependence on its position.

19 Claims, 4 Drawing Sheets (51) Int. Cl.
*G02B 26/00* (2006.01)
*F21S 8/10* (2006.01)
*F21V 9/10* (2006.01)
*F21V 14/04* (2006.01)
*F21K 9/62* (2016.01)
*F21K 9/64* (2016.01)
*F21K 9/65* (2016.01)
*G02B 26/08* (2006.01)
*F21Y 115/30* (2016.01)
*F21Y 115/10* (2016.01)

(52) U.S. Cl.
CPC ......... *F21S 48/115* (2013.01); *F21S 48/1757* (2013.01); *F21V 9/10* (2013.01); *F21V 14/04* (2013.01); *G01N 21/8806* (2013.01); *G02B 26/007* (2013.01); *F21S 48/328* (2013.01); *F21Y 2115/10* (2016.08); *F21Y 2115/30* (2016.08); *G02B 26/0833* (2013.01)

(58) Field of Classification Search
CPC . F21V 9/10; F21V 14/04; F21S 48/115; F21S 48/1757; F21S 48/328; G01N 21/8806; G02B 26/007; G02B 26/0833
USPC .................................................. 362/259, 84
See application file for complete search history.

(56) References Cited

U.S. PATENT DOCUMENTS

| | | |
|---|---|---|
| 2011/0044046 A1 | 2/2011 | Abu-Ageel |
| 2011/0249460 A1 | 10/2011 | Kushimoto |
| 2014/0254130 A1* | 9/2014 | Mehl ..................... G03B 33/08 362/84 |
| 2014/0355240 A1* | 12/2014 | Farchtchian ........... H04N 9/315 362/84 |

* cited by examiner

LIGHTING DEVICE WITH A PUMP LASER ROW AND METHOD FOR OPERATING SAID LIGHTING DEVICE

RELATED APPLICATIONS

The present application is a national stage entry according to 35 U.S.C. §371 of PCT application No.: PCT/EP2013/053013 filed on Feb. 14, 2013, which claims priority from German application No.: 102012203442.0 filed on Mar. 5, 2012, and is incorporated herein by reference in its entirety.

TECHNICAL FIELD

Various embodiments relate to a lighting device with a pump laser row and a phosphor arrangement, which is irradiated by the pump laser row. Furthermore, various embodiments relate to a method for operating this lighting device.

The term pump laser row is to be understood in the context of the disclosure to mean that at least two, or preferably more, pump lasers are arranged adjacent to one another in a row. The purpose of such a pump laser row is to generate a row or line of multiple pump laser beam spots for the irradiation of phosphors. The disclosure is usable in particular for projection devices, for example, for film and video projection, in industrial and medical image recognition, in technical and medical endoscopy, for light effects in the entertainment industry, for medical irradiation, and in the automotive field, in particular for headlights for motor vehicles.

BACKGROUND

Light sources of higher luminance are used in greatly varying fields, for example, in endoscopy and also in projection devices, wherein gas discharge lamps are presently most widely distributed. In lighting applications, for example, projection or endoscopy, based on the fundamentally known LARP ("laser activated remote phosphor") technology, a phosphor is irradiated by a laser. The laser radiation incident on the phosphor is partially converted by the phosphor by means of wavelength conversion into a wavelength-converted useful light and is partially scattered without a wavelength conversion.

In particular for video projection, the phosphors for the projector color channels red, green, and blue are typically applied to a rotating wheel, to distribute the laser power over a larger surface in chronological average and therefore to reduce the phosphor degradation.

Laser radiation is currently typically used in LARP technology. However, in the scope of the present disclosure, the term LARP is to be generalized such that other pump radiation sources suitable for phosphor excitation having comparable radiation properties as a laser, in particular its lesser beam divergence, are also included, for example, superluminescent diodes, optionally with or without downstream optics.

Document US 2011/0249460 A1 discloses a headlight for automobiles, using which various light distributions may be generated on the road. Two lasers are provided for this purpose, which each emit on a rectangular phosphor tablet via an associated MEMS mirror (MEMS: micro-electromechanical system). Each MEMS mirror can oscillate in two axes, whereby the two laser beams can in principle excite any point on the phosphor panel to luminescence. Depending on the desired light distributions, for example, distance light, traveling light, or curve light, at least one of the two lasers scans the phosphor panel in a corresponding irradiation pattern. With the aid of a projection optical system, the illumination pattern resulting from the irradiation pattern is projected from the phosphor panel onto the road. For specific lighting scenarios, both lasers having their associated mirror can also be in operation simultaneously, for example, for driving light with simultaneous curve light. In the event of failure of a laser-mirror pair, the remaining laser-mirror pair can also execute at least the basic functions alone.

SUMMARY

Various embodiments provide a lighting device based on LARP technology. One aspect in this case is the most compact possible structural form. A further aspect is to dispense with rotating components. Still a further aspect is the possibility of color changes of the light generated by the lighting device.

Various embodiments provide a lighting device with a pump laser row and a phosphor arrangement, wherein the pump laser row is designed to emit pump laser radiation for irradiating the phosphor arrangement, the phosphor arrangement has at least two different phosphors, which can be irradiated with the pump laser radiation and emit this pump laser radiation again at least partially and converted in wavelength differently in each case, and a movable mirror, which is designed to reflect the pump laser radiation of the pump laser row in a targeted manner on the phosphors in dependence on its position.

In addition, various embodiments provide a method for operating the lighting device.

The basic idea of the disclosure is to project a plurality of pump laser beam spots in a row adjacent to one another on a partial region of a phosphor pattern made of at least two different phosphors and to move this pump laser beam spot row with the aid of a movable mirror over the phosphor pattern, in order to generate mixed light in this manner from the pump laser radiation components which are converted in wavelength differently in chronological succession.

The luminous fluxes and also luminance typical for the applications mentioned at the outset may be achieved by way of a suitable selection of pump laser beam spots. Since the power density per unit area in a laser beam spot typically does not decrease abruptly but rather continuously from its center to the outside, it can be advantageous for reasons of efficiency if each pump laser beam spot slightly overlaps with its adjacent spots in the row on both sides, to achieve the most uniform possible power density per unit area on the irradiated phosphor along the pump laser beam spot row. Stronger or even complete overlap of all pump laser beam spots is opposed by excessively strong stress or even destruction of the respective irradiated phosphor, however. Rather, it is preferable for efficiency reasons for the pump laser beam spot row to have a longitudinal extension which is essentially equal to that of the corresponding longitudinal extension of the phosphor pattern. In addition, this has the advantage that, in contrast to the scanning of a single laser beam spot over a phosphor surface area according to the line jump method known according to the prior art, according to the present disclosure, only a single tilt axis is required for the tilt mirror instead of two, to be able to scan the pump laser beam spot row completely over the entire phosphor pattern.

Using this concept, lighting devices may be implemented which are suitable in particular also for projection applications based on both DLP (digital light processing from Texas Instruments) and also LCD (liquid crystal display) image generation units and which are very compact in comparison to conventional LARP systems having phosphor wheel and do not have any rotating components.

The pump laser radiation, which is emitted by a pump laser row, for example, a laser diode row, and is reflected from the mirror, thus scans the different phosphors of the phosphor arrangement during the movement or tilting of the mirror.

In a preferred embodiment, the different phosphors of the phosphor arrangement are preferably implemented in the form of phosphor strips and are arranged adjacent to one another, i.e., they form a strip-shaped phosphor pattern. In particular, ceramic phosphors are suitable for this purpose. By tilting the mirror, the pump laser beam spot row is moved over the phosphor strips, which correspondingly convert the pump laser radiation in wavelength.

The pump laser row is preferably aligned so that the pump laser radiation of the pump laser row forms a pump laser beam spot row on the phosphor strips, i.e., the pump laser beam spot row is aligned parallel to the phosphor strips.

In addition to a strip-shaped phosphor pattern, in principle other phosphor patterns are also suitable. For rapid color control, however, a strip-shaped phosphor pattern offers advantages, since it is geometrically adapted to the similarly also "strip-shaped" pump laser beam spot row.

In addition, it is advantageous to arrange the individual pump lasers of the pump laser row so that the respective pump laser beam spots thereof are superimposed in as spatially congruent a manner as possible on the mirror. This has the advantage that the mirror must then only have approximately the size of a single pump laser beam spot, instead of an entire pump laser beam spot row. The minimum size of the mirror is thus independent of the number of the individual pump lasers of the pump laser row. The mirror can preferably be implemented as a MEMS mirror (MEMS: micro-electromechanical system). Because of the small dimensions and therefore small mass of a MEMS mirror, tilt frequencies of several kilohertz are possible without problems. A chronologically averaged mixed light may be generated in this manner for the human eye, which is very sluggish in comparison thereto. Rapid color changes may thus also be implemented by suitable modulation of the tilt angle and/or the tilt frequency.

Preferably, an optical light mixer, for example, an optical system based on total internal reflection (TIR), is provided for mixing the pump laser radiation, which is converted in wavelength differently in each case by the phosphors, i.e., the colored light components generated by phosphor conversion. In this case, the optical light mixer is arranged between the pump laser row and the phosphor pattern, preferably very close above the phosphor pattern if the phosphor pattern is designed for usage in reflection. In this case, the component of the pump radiation, which is backscattered or diffusely reflected from the phosphor pattern and is converted in wavelength, is used for generating the additive mixed light. The incidence of the pump radiation and the collection of the colored light components generated by wavelength conversion are thus performed in this case on the same side of the phosphor pattern. It is ensured by the spatial proximity of the optical light mixer that the colored light components, which are typically scattered in a Lambert distribution and are converted in wavelength, are efficiently collected by this light mixer and are thoroughly mixed or spatially balanced on their path through the light mixer. The advantage in this so-called reflection mode is that the rear side of the phosphor pattern can be cooled without problems, for example, in that the phosphor pattern is arranged on a cooling body.

Alternatively, the phosphor pattern can also be designed for usage in transmission. The optical light mixer is then arranged on its rear side, i.e., on the side of the phosphor pattern opposite to the incident pump radiation. In this case, the radiation components, which pass through the phosphors and are at least partially converted in wavelength thereby, are collected and mixed by the optical light mixer. In this case, the phosphor pattern—except for the convection and thermal radiation—can only be cooled via an enclosing frame or, for example, an air stream. In contrast, a cooling arrangement as in the reflection mode is not possible.

The pump radiation is preferably in the ultraviolet (UV) or blue (B) spectral range. Therefore, converted light typically having longer wavelengths (down conversion) and having greater spectral bandwidth than the pump laser radiation may be produced via suitable phosphors, which are known per se, in particular if needed also red (R), green (G), and blue (B) light, for example, to thereby generate white mixed light together.

The method according to the present disclosure for operating a lighting device with a pump laser row, a movable mirror, and a phosphor arrangement, wherein the phosphor arrangement has at least two different phosphors which are capable of emitting the pump laser radiation of the pump laser row again at least partially converted in wavelength, differently in each case, includes at least the following method steps:

irradiating the mirror with the pump laser beams of the pump laser row, moving the mirror into a position which is suitable for the targeted irradiation of a subregion of the phosphor arrangement with the pump laser beams reflected on the mirror, so that the pump laser beams form a laser beam spot row on the subregion.

In one advantageous embodiment of the method, the mirror is additionally moved so that the laser beam spot row scans the various phosphors of the phosphor arrangement.

In a further advantageous embodiment, the various phosphors are preferably implemented as phosphor strips. In addition, the pump laser beam spot row is aligned parallel to the phosphor strips. The number, diameter, and arrangement of the pump laser beam spots are preferably adapted to the phosphor strips so that the pump laser beam spot row completely covers the phosphor strips, at least considered in the longitudinal extension thereof. The tilt mirror must thus only be moved in one axis to scan the phosphor strips completely. Rapid color control of the mixed light may thus be achieved via a modulation of the tilt angle and/or the tilt frequency of the mirror and/or the power of the pump laser row.

BRIEF DESCRIPTION OF THE DRAWINGS

In the drawings, like reference characters generally refer to the same parts throughout the different views. The drawings are not necessarily to scale, emphasis instead generally being placed upon illustrating the principles of the disclosed embodiments. In the following description, various embodiments described with reference to the following drawings, in which.

DETAILED DESCRIPTION

The following detailed description refers to the accompanying drawing that show, by way of illustration, specific details and embodiments in which the disclosure may be practiced.

Figure 1:
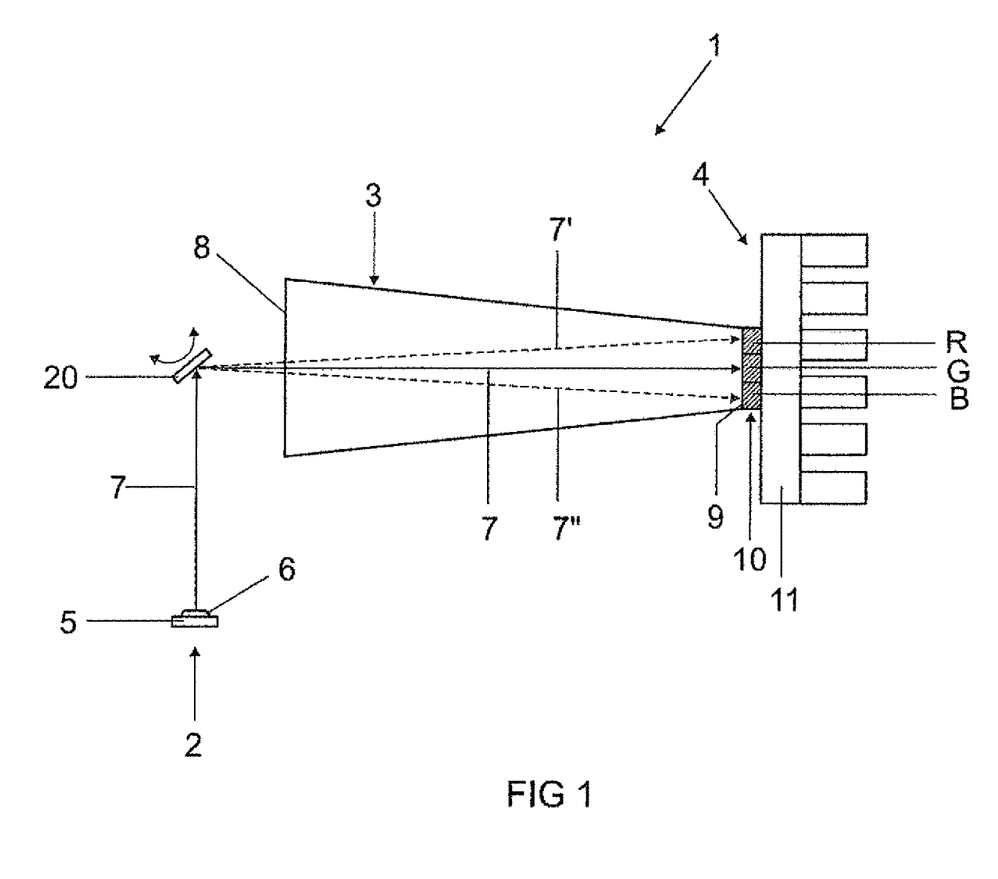
FIG. 1 shows an embodiment of the lighting device according to the present disclosure.
Figure 2:
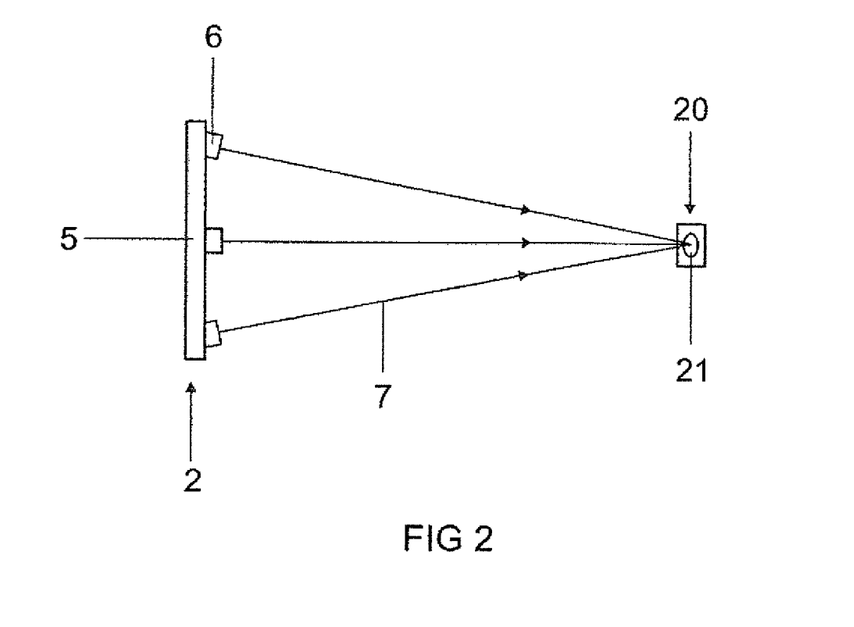
FIG. 2 shows the pump laser row and the MEMS tilt mirror from FIG. 1.
Figure 3:
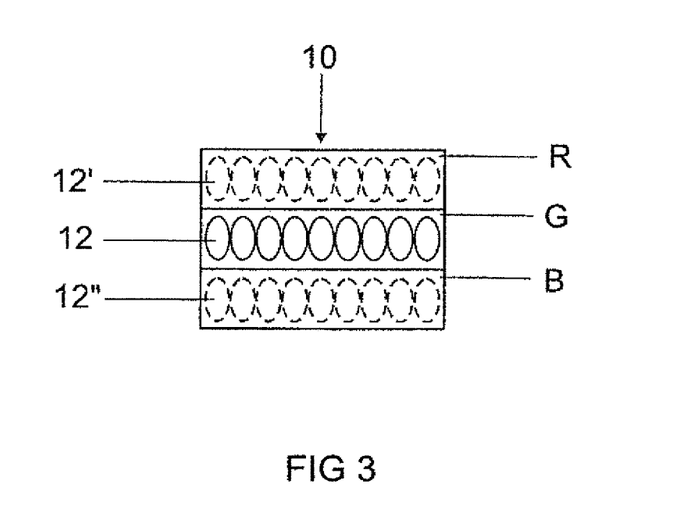
FIG. 3 shows the phosphor layer from FIG. 1.

FIG. 1 schematically shows a simplified embodiment of a lighting device 1 according to the present disclosure. The lighting device 1 has a pump laser row 2, a movable single-axis MEMS tilt mirror 20, an oblong optical light mixer 3, and a phosphor arrangement 4. The pump laser row 2 consists of a carrier 5, on which nine blue laser diodes 6 (emission wavelength approximately 405 nm) are arranged in a row. In the view shown in FIG. 1, the pump laser row 2 extends into the plane of the drawing, so that only the first laser diode 6 of the row is visible. In this context, reference is also made to FIG. 2, which shows the pump laser row 2 in a plane perpendicular thereto. For the sake of simplicity, however, only three of the total of nine laser diodes are shown in FIG. 2. It is nonetheless recognizable that the laser diodes are oriented toward the MEMS tilt mirror 20 in such a manner that the laser beam spots of the individual laser diodes 6 are superimposed on the MEMS tilt mirror 20 to form a shared laser beam spot 21. The laser diodes 6 are thus arranged increasingly tilted from the center to the outside so that their laser beams 7, which are incident diagonally to one another (symbolized in FIG. 2 by the three arrows), meet on the MEMS tilt mirror 20. This has the advantage that the MEMS tilt mirror 20 can be designed to be significantly smaller than if the nine laser diodes 6 would form a row of nine separate laser beam spots on the mirror in the event of laser beam guiding parallel to one another. Thus, because only a small mirror surface area is necessary due to the overlay of the laser beam spots, the mass of the MEMS tilt mirror 20 can be kept small, which is favorable in particular during rapid tilt movements. After the reflection on the MEMS tilt mirror 20, the laser beams 7 diverge again in accordance with the optical reflection law, so that the laser beam spots separate again with increasing distance from the MEMS tilt mirror 20 (not shown). As is recognizable in FIG. 1, the laser beams 7 of the nine laser diodes 6 enter the oblong light mixer 3 at a first end 8 and exit again at its other end 9. After the other end 9 of the light mixer 3, a segmented phosphor layer 10 follows, which is approximately 40 μm thick, and which is arranged on a cooling element 11 having cooling ribs, to thus together form the phosphor arrangement 4. The cooling element consists, for example, of aluminum, copper, silver, graphite, sapphire ($Al_2O_3$), diamond, silicon carbide, magnesium, and/or iron. Furthermore, the cooling body can also have ceramics such as AlN and/or alloys, for example, aluminum alloys or brass. Depending on the tilt angle of the MEMS tilt mirror 20, the laser beams 7 are incident after passing the light mixer 3 on corresponding regions of the phosphor layer 10 and form a laser beam spot row thereon (not recognizable in FIG. 1, since the phosphor layer 10, similarly to the laser row 2, extends into the plane of the drawing in the view shown in FIG. 1). FIG. 3 schematically shows a top view of the phosphor layer 10 having a laser beam spot row 12, corresponding to a middle position of the MEMS tilt mirror 20. The phosphor layer 10 consists of three strip-shaped phosphors R, G, B, which are arranged parallel and adjacent to one another. In this case, there is a red phosphor (R), for example, Calsin: $CaAlSiN_3$:Eu, a green phosphor (G), for example:

YAG: $Ce(Y_{0.96}Ce_{0.04})_3Al_{3.75}Ga_{1.25}O_{12}$, and a blue phosphor (B), for example:

$BaMgAl_{10}O_{17}$:$Eu^{2+}$.

The above-mentioned phosphors are to be understood solely as examples. In addition, numerous further suitable phosphors are usable for the present disclosure. Depending on the application, those having comparable conversion spectrum as those mentioned, i.e., red, green, and blue, come into consideration or also those having another conversion spectrum, for example, yellow, mint green, etc., wherein the generation of white mixed light or also colored mixed light is possible.

The laser beam spot row 12 is generated on the middle phosphor strip G in accordance with the middle position of the MEMS tilt mirror 20. For this purpose, the laser row 2 is arranged spatially matching with the phosphor strips R, G, B, so that the laser beam spot row is oriented parallel to the phosphor strips. In addition, the diameters of the individual laser beam spots of the laser beam spot row and the longitudinal extension of the laser beam spot row are adapted to the geometric dimensions of the phosphor strips so that the laser beam spot row essentially overlays the respective phosphor strip. At laser beam spot diameters typical for laser diodes (typically defined as the diameter with which approximately 86% of the total laser power is included) in the range of several hundred micrometers, for example, 600 μm, the length of the phosphor strips, depending on the number of laser diodes used in the laser diode row, is typically in the range of several millimeters. If a light having a significantly greater longitudinal extension is required, a plurality of these lighting devices can also be arranged modularly in a row. The laser beam spots do not necessarily have to directly adjoin one another, as shown in FIG. 3, but rather can also slightly overlap (not shown), for example, with a corresponding number of laser diodes, to achieve a more uniform power density distribution per unit area along the laser beam spot row. For suitable shaping of the individual pump laser beams, primary and/or secondary optics can be used (not shown). In an upper and lower position of the MEMS tilt mirror, the laser beam spot row is accordingly generated on the upper phosphor strip R or lower phosphor strip B, respectively—indicated by the dashed laser beams 7', 7" in FIG. 1 or the dotted laser beam spot rows 12', 12" in FIG. 3. In any case, the laser radiation is converted in wavelength by the respective phosphor strips R, G, B. In an advantageous operating mode, the MEMS tilt mirror 20 oscillates at a frequency in the kilohertz range between the upper and lower positions, so that the laser beam spot row 12 repeatedly scans the three phosphor strips R, G, B from top to bottom. A chronologically averaged mixed light is thus generated for the human eye—because of its inertia. The present disclosure is also suitable for further processing in imaging devices (not shown), since the possible line frequency of several kilohertz (kHz) is well above the typical image repetition frequency of 25 Hz or 50/60 Hz. Depending on the phosphors used and more precise activation of the MEMS tilt mirror 20, for example, white mixed light of various color temperatures or also colored light may thus be generated. The optical light mixer 3 is used, in addition to the collection of the component of the pump laser radiation which is back-scattered or diffusely reflected from the phosphors and converted in wavelength, also for the spatial balancing thereof. For this purpose, the optical light mixer 3 is implemented as a TIR optic and essentially consists of a conical glass rod having octagonal cross section. The colored light components which are chronologically back-scattered in succession by the phosphors R, G, B are totally reflected multiple times within the light mixer 3 at the interface to the surroundings and therefore spatially balanced. To avoid interference of the decoupled mixed light due to the MEMS tilt mirror arranged approximately in the middle in front of the first end 8 of the optical light mixer 3, the mixed light can be decoupled to the side by means of a dichroic mirror (not shown), which is arranged tilted between laser row 2 and light mixer 3. For this purpose, the side facing toward the light mixer is coated using an interference layer, which reflects the mixed light and transmits the blue narrowband laser radiation.

Figure 4:
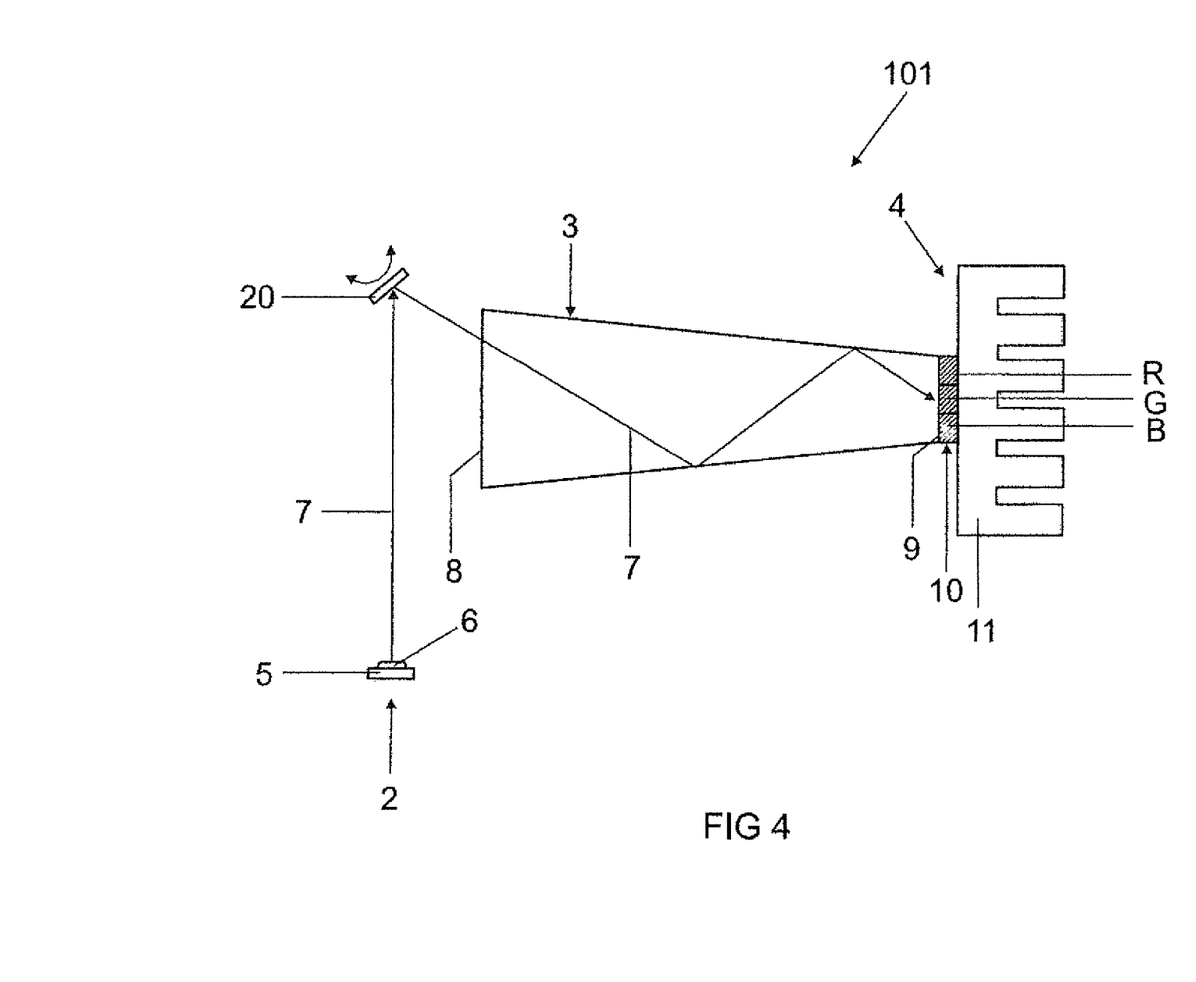
FIG. 4 shows a second embodiment of the lighting device according to the present disclosure.

An alternative preferred embodiment of the lighting device according to the present disclosure is schematically shown in FIG. 4. The lighting device 101 only differs from the lighting device 1 shown in FIG. 1 in that the MEMS tilt mirror 20 is not arranged in the middle in front of the first end 8 of the optical light mixer 3, but rather outside thereof, offset transversely. The wavelength-converted mixed light can thus be decoupled unobstructed from the first end 8 of the optical light mixer 3. A dichroic decoupling mirror, as in the embodiment shown in FIG. 1, is not required here. The transversely offset arrangement of the MEMS tilt mirror 20 causes, on the other hand, the pump laser beams to be incident at an oblique angle on the first end 8 of the optical light mixer 3. The pump laser beams are therefore no longer incident directly, but rather via one or more internal reflections within the TIR light mixer 3 on the phosphor layer 10. With suitable design, the laser beam spot row generated by the laser row 2 may nonetheless scan the phosphor strips R, G, B with the aid of the MEMS tilt mirror 20.

Figure 5:
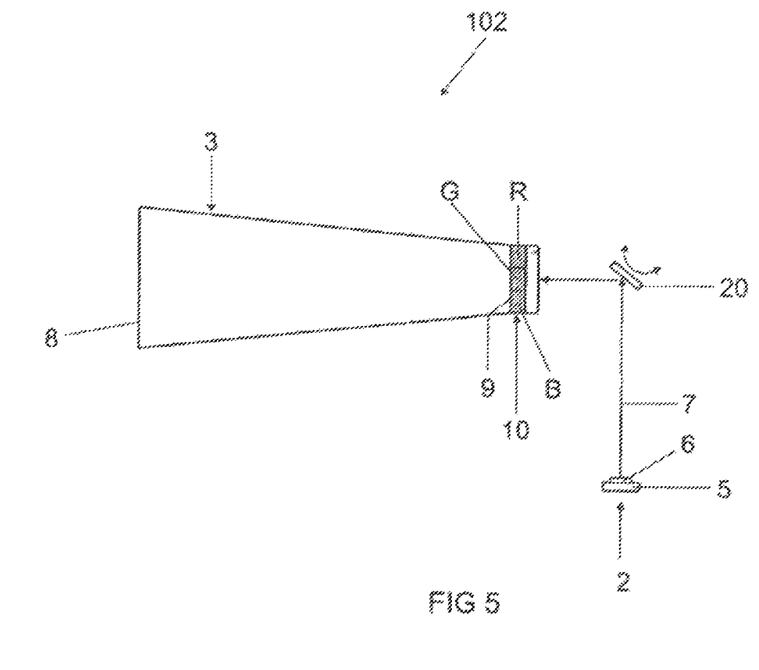
FIG. 5 shows a third embodiment of the lighting device according to the present disclosure.

Finally, FIG. 5 shows a third embodiment. In the lighting device 102, the phosphor layer 10 having the three phosphors R, G, B is not irradiated through the optical light mixer 3, but rather from the "rear side". For this purpose, the MEMS tilt mirror 20 is arranged on the side of the phosphor layer 10 facing away from the light mixer 3. The phosphor layer 10 is thus not operated in reflection here, as in the embodiments according to FIG. 1 and FIG. 4, but rather in transmission. However, a cooling body on the "rear side" of the phosphor layer must necessarily be omitted here. The laser beam spot row generated by the laser row 2 is specifically incident on the "rear side" of the transparent phosphor layer 10 via the tilt mirror 20. The wavelength-converted colored light is emitted via the "front side" of the phosphor layer 10, collected there by the optical light mixer 3, and spatially balanced. A dichroic filter applied to the "rear side" of the transparent phosphor layer 10 prevents back-scattering of the pump laser beams 7.

While the disclosed embodiments have been particularly shown and described with reference to specific embodiments, it should be understood by those skilled in the art that various changes in form and detail may be made therein without departing from the spirit and scope of the disclosed embodiments as defined by the appended claims. The scope of the disclosed embodiments is thus indicated by the appended claims and all changes which come within the meaning and range of equivalency of the claims are therefore intended to be embraced.

The invention claimed is:

1. A lighting device comprising a pump laser row and a phosphor arrangement, wherein
    the pump laser row is designed for the purpose of emitting pump laser radiation for the irradiation of the phosphor arrangement,
    the phosphor arrangement has at least two different phosphors, which can be irradiated with the pump laser radiation and emit the pump laser radiation again at least partially and converted in wavelength differently in each case,
        wherein the different phosphors of the phosphor arrangement implemented in the form of phosphor strips which are arranged parallel and adjacent to one another; and
        wherein the pump laser aligned so that the pump laser radiation of the pump laser row forms a pump laser beam spot on the phosphor strips, and
    a movable mirror, which is designed for the purpose of reflecting the pump laser radiation of the pump laser row in a targeted manner on the phosphors in dependence on its position.

2. The lighting device as claimed in claim 1, wherein the pump laser radiation successively scans the different phosphors during the movement of the mirror.

3. The lighting device as claimed in claim 1, wherein the mirror is tiltable in relation to the incident pump laser radiation and the pump laser radiation can be guided onto the phosphor strips of the phosphor arrangement by tilting the mirror.

4. The lighting device as claimed in claim 1, wherein the individual pump lasers of the pump laser row are arranged so that the respective pump laser beam spots thereof overlay in a spatially congruent manner on the mirror.

5. The lighting device as claimed in claim 1, wherein the mirror is only designed for one tilt axis.

6. The lighting device as claimed in claim 1, wherein the mirror is implemented as a MEMS mirror.

7. The lighting device as claimed in claim 1, wherein individual pump lasers of the pump laser row are implemented as laser diodes.

8. The lighting device as claimed in claim 1, further comprising an optical light mixer for mixing the radiation, which is converted in wavelength differently by each of the phosphors.

9. A method for operating a lighting device comprising a pump laser row, a movable mirror, and a phosphor arrangement, wherein the phosphor arrangement has at least two different phosphors, which are capable of at least partially emitting the pump laser radiation of the pump laser row again, converted in wavelength differently in each case,
    the method comprising:
        irradiating the mirror with pump laser beams of the pump laser row, moving the mirror into a position which is suitable for the targeted irradiation of a subregion of the phosphor arrangement with the pump laser beams reflected on the mirror, so that the pump laser beams form a pump laser beam spot row on the subregion, wherein
        the various phosphors are implemented as phosphor strips and the phosphor strips and the pump laser beam spot row are aligned parallel and adjacent to one another.

10. The method as claimed in claim 9, further comprising: moving the mirror to scan laser beam spot row over the various phosphors of the phosphor arrangement.

11. The method as claimed in claim 10, wherein at least one of the tilt angle, the tilt frequency of the mirror and the power of the pump laser row is modulated.

12. The method as claimed in claim 9, wherein the mirror is only tilted in one tilt axis.

13. A lighting device comprising a pump laser row and a phosphor arrangement, wherein
the pump laser row is designed for the purpose of emitting pump laser radiation for the irradiation of the phosphor arrangement,
the phosphor arrangement has at least two different phosphors, which can be irradiated with the pump laser radiation and emit the pump laser radiation again at least partially and converted in wavelength differently in each case, and
a movable mirror, which is designed for the purpose of reflecting the pump laser radiation of the pump laser row in a targeted manner on the phosphors in dependence on its position,
wherein individual pump lasers of the pump laser row are implemented as laser diodes oriented toward the movable mirror and arranged increasingly tilted from the center to the outside.

14. The lighting device as claimed in claim 13, wherein the pump laser radiation successively scans the different phosphors during the movement of the mirror.

15. The lighting device as claimed in claim 13, wherein the different phosphors of the phosphor arrangement are implemented in the form of phosphor strips and arranged parallel and adjacent to one another.

16. The lighting device as claimed in claim 15, wherein the mirror is tiltable in relation to the incident pump laser radiation and the pump laser radiation can be guided onto the phosphor strips of the phosphor arrangement by tilting the mirror.

17. The lighting device as claimed in claim 15, wherein the pump laser row is aligned so that the pump laser radiation of the pump laser row forms a pump laser beam spot row on the phosphor strips.

18. The lighting device as claimed in claim 17, wherein the individual pump lasers of the pump laser row are arranged so that the respective pump laser beam spots thereof overlay in a spatially congruent manner on the mirror.

19. The lighting device as claimed in claim 13, further comprising an optical light mixer for mixing the radiation, which is converted in wavelength differently by each of the phosphors.

* * * * *

UNITED STATES PATENT AND TRADEMARK OFFICE
CERTIFICATE OF CORRECTION

PATENT NO. : 9,677,743 B2
APPLICATION NO. : 14/382785
DATED : June 13, 2017
INVENTOR(S) : Kroell It is certified that error appears in the above-identified patent and that said Letters Patent is hereby corrected as shown below:

In the Claims

Column 5, Line 55: Please insert the number --11-- between the words "element" and "consists".

Column 6, Line 7: Please insert a space before and after the brackets.

Column 6, Line 7: Please delete the letter "ε" and write the number --6-- in place thereof.

Signed and Sealed this
First Day of August, 2017

Joseph Matal
*Performing the Functions and Duties of the
Under Secretary of Commerce for Intellectual Property and
Director of the United States Patent and Trademark Office*